(12) United States Patent
Toriihara

(10) Patent No.: US 11,012,671 B2
(45) Date of Patent: May 18, 2021

(54) INFORMATION PROCESSING APPARATUS, IMAGE CAPTURING APPARATUS, AND INFORMATION PROCESSING METHOD

(71) Applicant: CANON KABUSHIKI KAISHA, Tokyo (JP)

(72) Inventor: Shigeru Toriihara, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/704,527

(22) Filed: Dec. 5, 2019

(65) Prior Publication Data

US 2020/0186766 A1   Jun. 11, 2020

(30) Foreign Application Priority Data

Dec. 10, 2018   (JP) .............................. JP2018-230778

(51) Int. Cl.
  *H04N 9/31*   (2006.01)
  *G16H 10/60*   (2018.01)
  *H04N 5/232*   (2006.01)
  *H04N 9/64*   (2006.01)

(52) U.S. Cl.
  CPC ........... *H04N 9/3182* (2013.01); *G16H 10/60* (2018.01); *H04N 5/23218* (2018.08); *H04N 9/646* (2013.01)

(58) Field of Classification Search
  CPC .. H04N 9/3182; H04N 5/23218; H04N 9/646; G16H 10/60
  See application file for complete search history.

(56) References Cited

U.S. PATENT DOCUMENTS

| | | | |
|---|---|---|---|
| 2008/0240558 A1* | 10/2008 | Li | H04N 1/00045 382/167 |
| 2008/0260218 A1* | 10/2008 | Smith | A61B 5/444 382/128 |
| 2008/0292151 A1* | 11/2008 | Kurtz | G16H 15/00 382/128 |
| 2008/0294017 A1* | 11/2008 | Gobeyn | A61B 5/442 600/301 |
| 2014/0056538 A1* | 2/2014 | Kokemohr | G06K 9/00536 382/274 |
| 2019/0301941 A1* | 10/2019 | Kawabata | H04N 1/46 |

FOREIGN PATENT DOCUMENTS

| | | | |
|---|---|---|---|
| JP | 11-19050 A | 1/1999 | |
| JP | H1119050 A * | 1/1999 | .............. A61B 5/00 |
| JP | 2007-174684 A | 7/2007 | |

* cited by examiner

*Primary Examiner* — Sarah Lhymn
(74) *Attorney, Agent, or Firm* — Canon U.S.A., Inc. IP Division

(57) ABSTRACT

An apparatus captures an image of an ID tag displaying printed ID information specific to a patient to acquire an ID-tag image, and acquires a color correction value from the ID-tag image. The color correction value is used to correct an image to be captured. The apparatus corrects a captured image of an affected area by using the color correction value.

12 Claims, 5 Drawing Sheets

INFORMATION PROCESSING APPARATUS, IMAGE CAPTURING APPARATUS, AND INFORMATION PROCESSING METHOD

BACKGROUND OF THE INVENTION

Field of the Invention

The aspect of the embodiments relates to an information processing apparatus, an image capturing apparatus, and an information processing method, and in particular, relates to a technique suitably used for correcting a captured image of a subject.

Description of the Related Art

Doctors and nurses can use image capturing apparatuses at medical sites. For example, a doctor or a nurse periodically captures an image of a wound in a skin or a decubitus ulcer of a bedridden person, who is confined to bed for a long time, by using an image capturing apparatus. When viewing an array of captured images, the doctor or the nurse can easily observe improvement or deterioration of such an affected area over time. The image capturing apparatus is suitable for examination of an affected area that changes in condition over a period ranging from days to years.

In the following description, a person who uses an image capturing apparatus, such as a doctor or a nurse, will be referred to as a user as necessary, and a captured image of an affected area will be referred to as an affected-area image as necessary. Accumulating affected-area images without any special processing may make it difficult for a user to find a target image or may cause the user to refer to a wrong image. Capturing affected areas without any special consideration results in variations in ambient light, for example, dark ambient light, bright ambient light, morning light, and sunset light. Variations in color tones of captured images of an affected area may make it difficult for a user to examine the affected area or may cause misdiagnosis.

Under the above-described background, Japanese Patent Laid-Open No. 2007-174684 discloses the following technique. A user is requested to capture an image of an identification (ID) tag assigned to a patient before capturing an image of an affected area of the patient. An input device identifies characters or a bar code on the ID tag of the patient. A computer checks input information against a database containing information concerning patients. An image capturing apparatus displays information acquired from the database and embeds the information in an affected-area image.

Japanese Patent Laid-Open No. 11-19050 discloses the following technique and the following image capturing apparatuses. The image capturing apparatuses are intended to be used for telemedicine. The image capturing apparatus on a transmission side captures an image of an affected area and a reference color sample to acquire an affected-area image. The image capturing apparatus on a reception side performs white balance correction so that the color of the reference color sample included in the affected-area image is close to the color of the actual reference color sample.

The technique disclosed in Japanese Patent Laid-Open No. 2007-174684 enables arrangement of affected-area images of one affected area of one patient by using patient information embedded in the affected-area images. However, there is no guarantee that the affected-area images have the same color tones. For a decubitus ulcer, for example, dermis, subcutaneous tissue, or necrosis is identified based on its color to determine whether the condition has improved or deteriorated. Unreliable color tones of an affected-area image cause a user to fail to determine whether a change in color of the affected area is a change over time or is caused by ambient light. Unfortunately, the user may fail to make a diagnosis or may make a wrong diagnosis.

According to the technique disclosed in Japanese Patent Laid-Open No. 11-19050, the image capturing apparatus on the transmission side and the image capturing apparatus on the reception side each need the reference color sample when an image of an affected area is captured. Installation of the reference color sample may become a special burden to users. Furthermore, as telemedicine and home medical care are being promoted, persons other than medical professionals are more likely to capture images of affected areas at sites other than medical institutions. In such a case, installation of the reference color sample may become a burden to each site.

SUMMARY OF THE INVENTION

An aspect of the embodiments provides an apparatus including at least one processor and at least one memory coupled to the processor storing instructions that, when executed by the processor, cause the processor to function as: a first acquiring unit configured to acquire a first color correction value based on a region having a reference color in an ID tag assigned to a subject in a captured image including the subject and the ID tag; and a correcting unit configured to correct an image of the subject with the acquired first color correction value.

Further features of the disclosure will become apparent from the following description of exemplary embodiments with reference to the attached drawings.

DESCRIPTION OF THE EMBODIMENTS

An exemplary embodiment of the disclosure will be described with reference to the drawings.

In this embodiment, for example, it is assumed that an image capturing apparatus and an image processing apparatus are used at a medical site. In this case, subjects of the image capturing apparatus include (affected areas of) patients. The image capturing apparatus periodically captures an image of, for example, a wound in a skin of a patient or a decubitus ulcer of a bedridden patient, who is confined to bed for a long time, and recodes the image. A user can easily observe improvement or deterioration of such an affected area over time when viewing an array of captured images. The image capturing apparatus and the image processing apparatus according to the embodiment are suitable for observation and treatment of, for example, an affected area that changes in condition for a period ranging from days to years. Furthermore, the embodiment is widely applicable to image capturing apparatuses for various applications in addition to the image capturing apparatus at a medical site.

Figure 1:
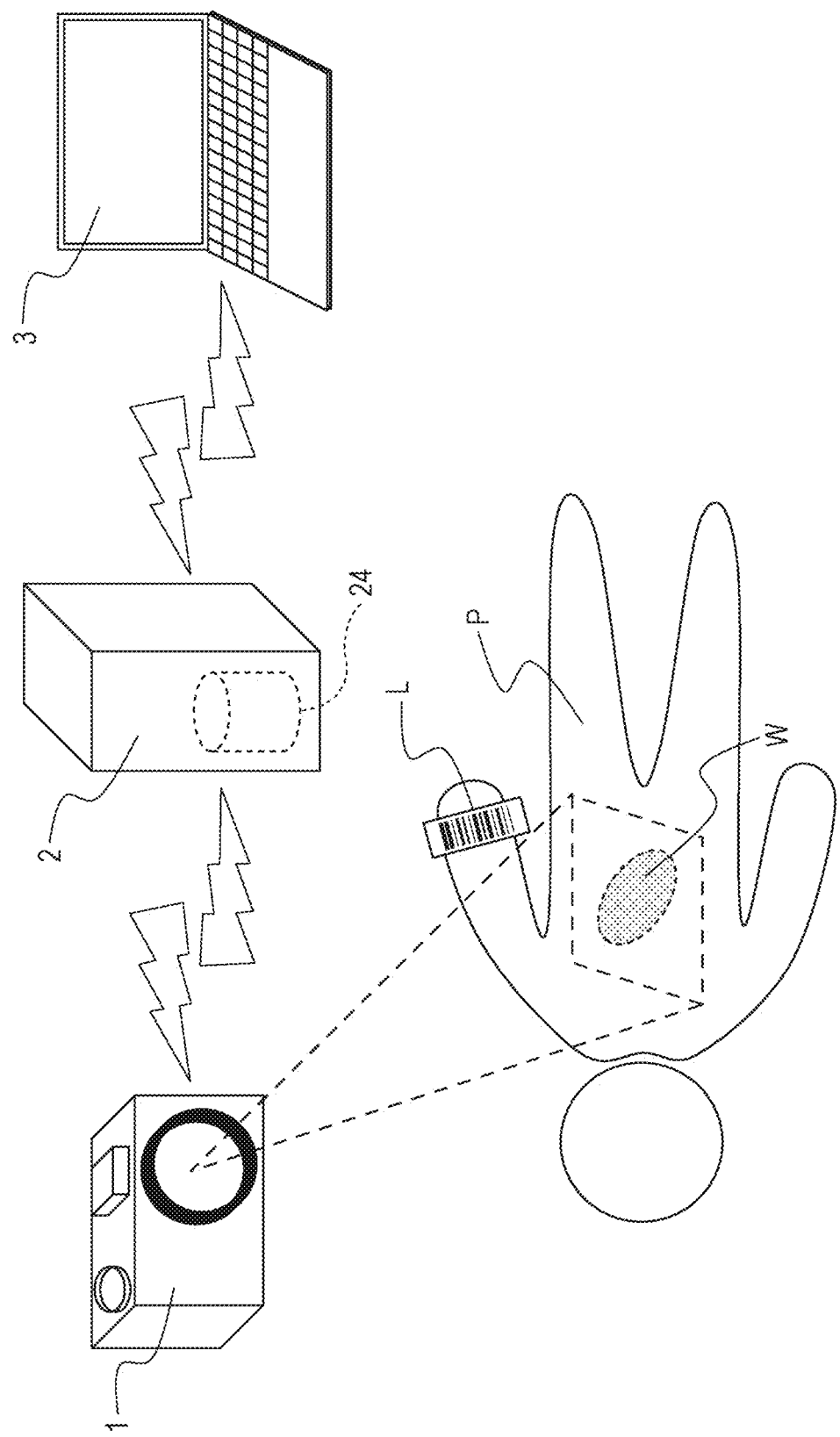
FIG. 1 is a diagram illustrating an exemplary configuration of an image processing system.

FIG. 1 illustrates an exemplary configuration of an image processing system. FIG. 1 illustrates an image capturing apparatus, an image processing apparatus, a display apparatus, a patient, an affected area, and an ID tag in a full view. In FIG. 1, an image capturing apparatus 1, an image processing apparatus 2, a display apparatus 3, a patient P, an affected area W, and an ID tag L can be visually identified. With the exemplary configuration of FIG. 1, the image processing system includes the image capturing apparatus 1, the image processing apparatus 2, and the display apparatus 3.

An exemplary manner in which a user uses the image capturing apparatus 1 will now be described with reference to FIG. 1. The image capturing apparatus 1, the image processing apparatus 2, and the display apparatus 3 are connected to each other through a communication link or line such that these apparatuses can transmit and receive information to and from each other. The user captures an image of the affected area W of the patient P and an image of the ID tag L with the image capturing apparatus 1. The image capturing apparatus 1 transmits the captured image (hereinafter, "affected-area image") of the affected area W and the captured image (hereinafter, "ID-tag image") of the ID tag L to the image processing apparatus 2.

The image processing apparatus 2 performs proper image processing on the affected-area image and the ID-tag image, and records the affected-area image and the ID-tag image subjected to the image processing onto a storage 24 included in the image processing apparatus 2.

The display apparatus 3 displays a group of affected-area images recorded on the storage 24 in response to a user operation on the display apparatus 3. The user can view the group of affected-area images recorded on the storage 24 to examine the affected area W.

In the exemplary configuration of FIG. 1, the image capturing apparatus 1, the image processing apparatus 2, and the display apparatus 3 are separate components. At least two of the image capturing apparatus 1, the image processing apparatus 2, and the display apparatus 3 may be combined as one apparatus.

Figure 2:
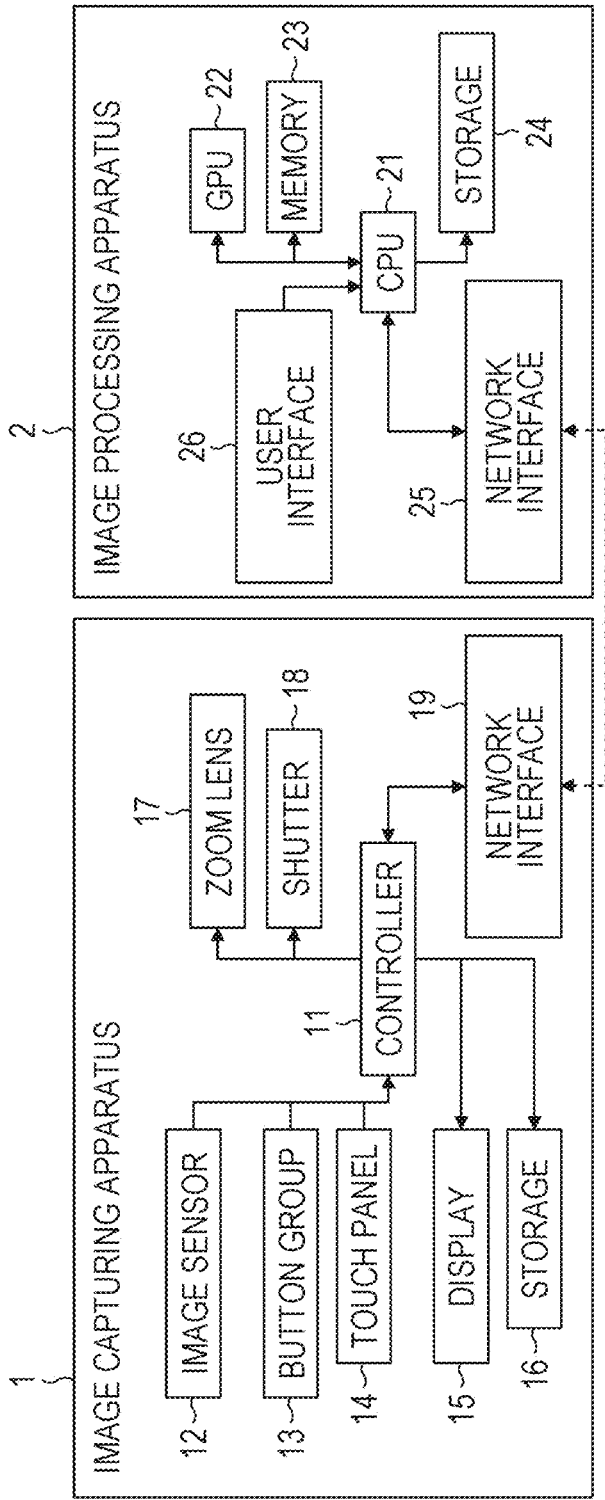
FIG. 2 is a diagram illustrating an exemplary configuration of an image capturing apparatus and that of an image processing apparatus.

FIG. 2 is a block diagram illustrating an exemplary configuration of the image capturing apparatus 1 and that of the image processing apparatus 2. Examples of the image capturing apparatus 1 include, but not limited to, a digital still camera, a digital movie camera, a cellular phone, and a tablet. Although the image capturing apparatus 1 can be a hand-held portable device that is easy for a user to carry, the image capturing apparatus 1 does not necessarily have to be a hand-held portable device. The image capturing apparatus 1 may be an industrial camera or a medical camera.

The exemplary configuration of the image capturing apparatus 1 will now be described with reference to FIG. 2. The image capturing apparatus 1 includes a controller 11, an image sensor 12, a button group 13, a touch panel 14, a display 15, a storage 16, a zoom lens 17, a shutter 18, and a network interface 19.

The controller 11 performs centralized control on information processing in the image capturing apparatus 1 to control the other units. The image sensor 12 converts incoming photons into an electrical signal. The button group 13 and the touch panel 14 receive a user operation. The display 15 displays, for example, an image or a parameter. The storage 16 temporarily or permanently stores data, such as an image. The zoom lens 17 adjusts the angle of view and the focus when an image is captured. The shutter 18 controls light entering the image sensor 12. The network interface 19 transmits and receives data, such as an image or an amount of control, to and from an external apparatus, for example, the image processing apparatus 2.

The exemplary configuration of the image processing apparatus 2 will now be described with reference to FIG. 2. The image processing apparatus 2 includes a central processing unit (CPU) 21, a graphics processing unit (GPU) 22, a memory 23, the storage 24, a network interface 25, and a user interface 26.

The CPU 21 performs centralized control on information processing in the image processing apparatus 2. The GPU 22 assists in processing, such as image quality improvement and image identification. The memory 23 stores temporary information that is being processed. The storage 24 temporarily or permanently stores data, such as an image. The user interface 26 includes pointing devices, such as a keyboard and a mouse, and receives a user operation. The network interface 25 transmits and receives data, such as an image or an amount of control, to and from an external apparatus, for example, the image capturing apparatus 1. In the embodiment, the network interface 25 is communicatively connected to the network interface 19 of the image capturing apparatus 1 and the display apparatus 3.

A configuration of the display apparatus 3 can be achieved by, for example, adding a computer display to the configuration of the image processing apparatus 2 in FIG. 2 or by using the display 15 included in the image capturing apparatus 1 in FIG. 2. A detailed description of the display apparatus 3 is omitted herein.

Figure 3:
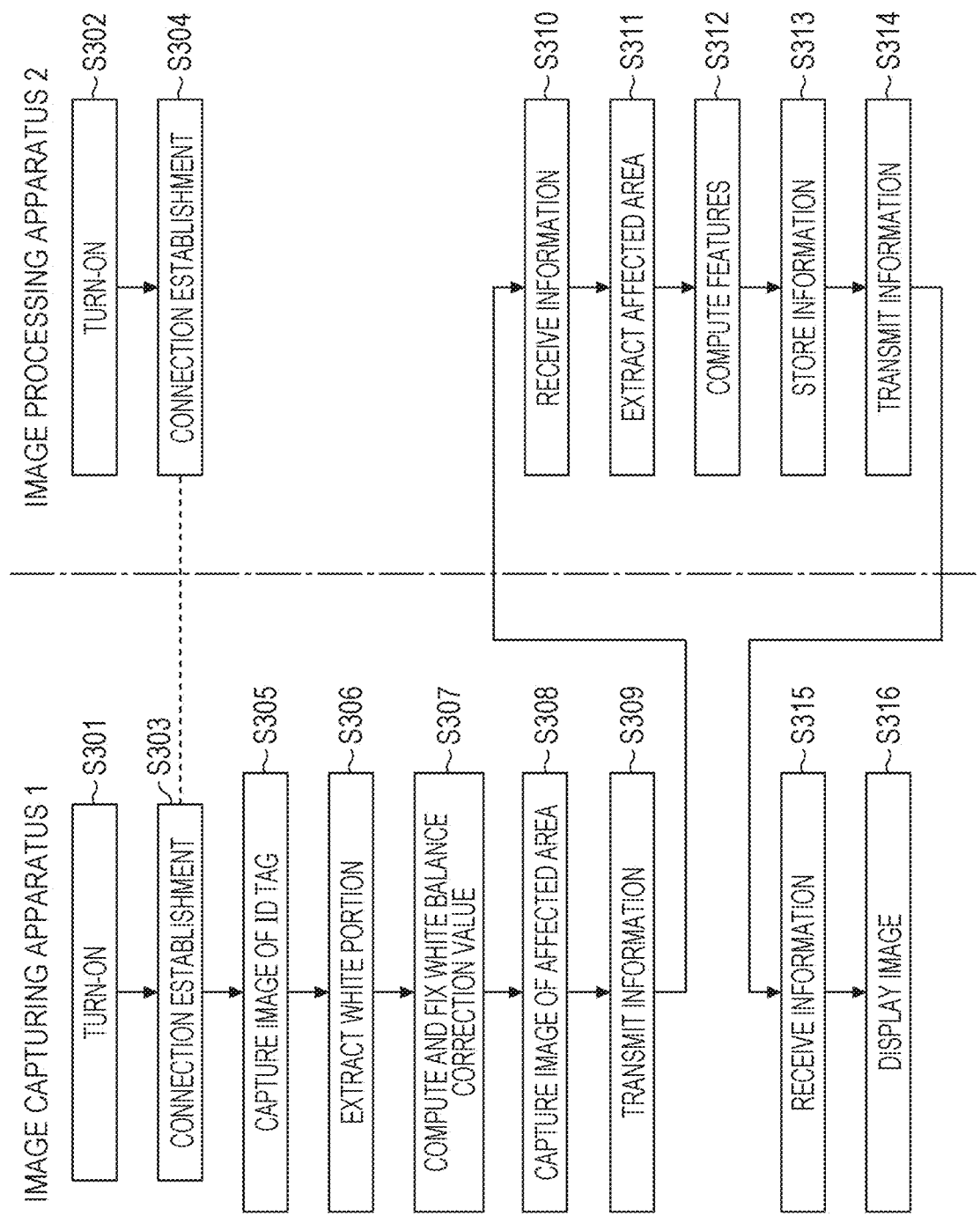
FIG. 3 is a flowchart illustrating a process executed by the image capturing apparatus and the image processing apparatus.

FIG. 3 is a flowchart illustrating an exemplary process executed by the image capturing apparatus 1 and the image processing apparatus 2. In FIG. 3, each reference numeral with "S" denotes step. For example, S301 denotes step 301.

In S301, a user operates the button group 13 (e.g., a power switch) to turn on the image capturing apparatus 1. In S302, a user operates the user interface 26 to turn on the image processing apparatus 2.

In S303 and S304, connection between the image capturing apparatus 1 and the image processing apparatus 2 is established, so that the apparatuses can transmit and receive information to and from each other.

In S305, the image capturing apparatus 1 captures an image of the ID tag L of the patient P in response to a user operation on the button group 13 (e.g., a release button). The image capturing apparatus 1 reads information (characters and a mark) on the ID tag L from the captured image to acquire information concerning the patient P.

In S306, the image capturing apparatus 1 extracts a white portion of the ID-tag image. The white portion of the ID-tag image is a region corresponding to a white portion of the ID tag L. The white portion of the ID-tag image is extracted based on, for example, the characters and the mark printed on the ID tag L.

In operations in S305 and S306, the information concerning the patient P on the ID tag L and a brightness value of the white portion of the ID-tag image are acquired. The ID-tag image does not necessarily have to be stored.

In S307, the image capturing apparatus 1 computes a white balance correction value with which the brightness value, acquired in S306, of the white portion of the ID-tag image can be corrected properly, and performs white balance correction processing.

In S308, the image capturing apparatus 1 captures an image of the affected area W in response to a user operation on the button group 13 (e.g., the release button) while the white balance correction value acquired in S307 remains fixed, thus acquiring the image of the affected area, or the affected-area image, subjected to the white balance processing based on the white portion of the ID-tag image.

In S309, the image capturing apparatus 1 transmits information including the information concerning the patient P acquired in S305, the white balance correction value acquired in S307, and the affected-area image acquired in S308 to the image processing apparatus 2.

In S310, the image processing apparatus 2 receives the information transmitted in S309.

In S311, the image processing apparatus 2 extracts the affected area W included in the affected-area image. The affected area W is discriminated from the skin of the patient P by using, for example, deductive image processing or segmentation using a pre-trained neural network.

In S312, the image processing apparatus 2 computes features of the affected area W based on the shape and color of the affected area W extracted in S311. For example, a long side and a short side of a minimum rectangle including the affected area W are used for examination of a decubitus ulcer. In this case, the lengths of the long and short sides are computed as features of the affected area W.

In S313, the image processing apparatus 2 associates the affected-area image, the white balance correction value, the shape and color of the affected area W, and the features of the affected area W with each other and stores this information into the storage 24. At this time, the image processing apparatus 2 uses the information concerning the patient P acquired in S305 and received in S310 to generate at least one of a folder name, a file name, and a tag so that the user can identify the patient P. Consequently, the affected-area image, the white balance correction value, the shape and color of the affected area W, and the features of the affected area W are stored such that the user can identify the information belonging to the patient P. If the image of the affected area captured by the image capturing apparatus 1 has already been subjected to white balance correction, the white balance correction value does not have to be stored. If the affected-area image and the white balance correction value are stored in association with each other, the white balance correction value upon image capture can be used as reference data to correct color tones of the affected-area image.

In S314, the image processing apparatus 2 transmits the information including the affected-area image, the shape and color of the affected area W, and the features of the affected area W to the image capturing apparatus 1.

In S315, the image capturing apparatus 1 receives the information transmitted in S314.

In S316, the image capturing apparatus 1 superimposes the shape of the affected area W and the features thereof on the affected-area image to produce an image and displays the produced image on the display 15. The user can determine a condition of the affected area W and identify the features by viewing the image displayed on the display 15. The affected-area image on which the shape of the affected area W and the features thereof are superimposed may be displayed on the display apparatus 3 instead of the image capturing apparatus 1.

The process illustrated by the flowchart of FIG. 3 is performed in the above-described manner.

FIGS. 4A to 4D are diagrams illustrating examples of the ID tag L of the patient P. Exemplary manners of using the ID tag L of the patient P will be described with reference to FIGS. 4A to 4D. Each of the ID tags L illustrated in FIGS. 4A to 4D displays ID information specific to the patient P in an environment where the patient P exists.

Figure 4A:
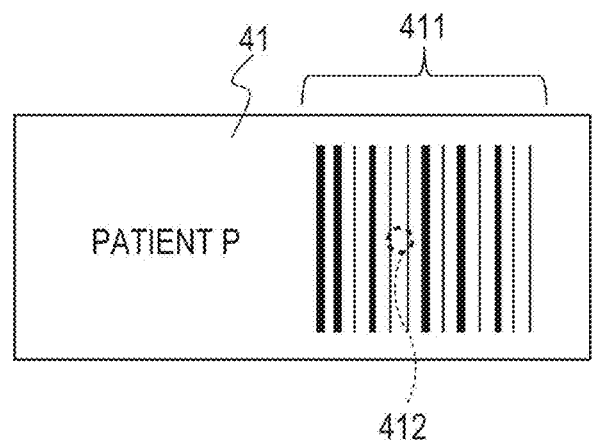
FIGS. 4A to 4D are diagrams each illustrating an ID tag of a patient.

FIG. 4A illustrates an example of an ID tag 41 intended to be attached to a wrist of the patient P. The ID tag 41 includes a white base and has a printed bar code 411 at least. In S305 in FIG. 3 described above, the image capturing apparatus 1 captures an image of the ID tag 41 having the bar code 411 to acquire an ID-tag image. The image capturing apparatus 1 identifies the bar code 411 included in the ID-tag image to acquire information concerning the patient P, for example, a number assigned to the patient P and the name of the patient P. The image capturing apparatus 1 also acquires a position of the bar code 411 in the ID-tag image.

The bar code 411 includes a white portion 412 between black portions. The image capturing apparatus 1 extracts the white portion 412 in S306, and computes a white balance correction value based on an RGB brightness value of the white portion 412 in S307. Thus, the image capturing apparatus 1 can obtain a white balance correction value that is likely to be suitable for correction from the captured image of such a white object under substantially the same ambient light as that for image capture of the affected area W in S308. White portions 412 at different positions may be used instead of a white portion 412 at a specific position. In this case, for example, a mean value of the RGB brightness values at the different positions is used to compute a white balance correction value. A representative value (e.g., a median) other than the mean value of the RGB brightness values at the different positions may be used to compute a white balance correction value.

Figure 4B:
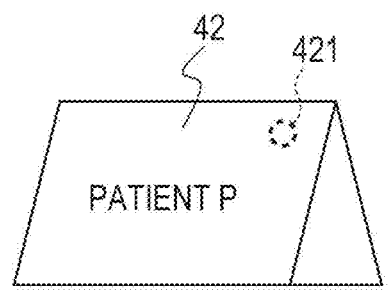

FIG. 4B illustrates an example of an ID tag 42 intended to be disposed adjacent to the patient P (for example, in the same room). The ID tag 42 includes a white base and has printed characters representing the name of the patient P at least. In S305 in FIG. 3 described above, the image capturing apparatus 1 captures an image of the ID tag 42 having the name of the patient P to acquire an ID-tag image. The image capturing apparatus 1 identifies the characters representing the name of the patient P included in the ID-tag image to acquire the name of the patient P as information concerning the patient P. The image capturing apparatus 1 also acquires a position of the printed name of the patient P in the ID-tag image.

The ID tag 42 includes a white portion 421 at a proper position relative to the name of the patient P, or a relative position based on the position of the name of the patient P. Examples of the proper relative position include a position at a predetermined distance from a bounding rectangle containing the name of the patient P in a predetermined direction. For example, each region between the characters representing the name of the patient P may be a white portion. The image capturing apparatus 1 extracts the white portion 421 in S306 and computes a white balance correction value based on an RGB brightness value of the white portion 421 in S307 in a manner similar to that in FIG. 4A. The white portion 421 may be located at any position without ink included in the printed name of the patient P. White portions 421 at different positions may be used.

Figure 4C:
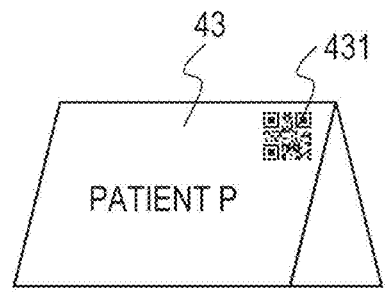

FIG. 4C illustrates an example of an ID tag 43, which is intended to be disposed adjacent to the patient P like the ID tag of FIG. 4B. The ID tag 43 includes a white base and has a printed two-dimensional code 431 at least. The image capturing apparatus 1 acquires information contained in the two-dimensional code 431 and the position of the two-dimensional code 431 in S305 in a manner similar to the case of the bar code 411 in FIG. 4A and the case of the name of the patient P in FIG. 4B. The image capturing apparatus 1 extracts a white portion in S306 and computes a white balance correction value based on an RGB brightness value of the white portion in S307 on the assumption that the white portion is located at a proper position relative to the two-dimensional code 431 in a manner similar to those in FIGS. 4A and 4B. For example, a blank portion of the two-dimensional code 431 or a region at a predetermined distance from a bounding rectangle containing the two-dimensional code 431 in a predetermined direction can be used as a white portion. The white portion may be located at any position without ink included in the two-dimensional code 431 and the printed name of the patient P. White portions at different positions may be used.

Figure 4D:
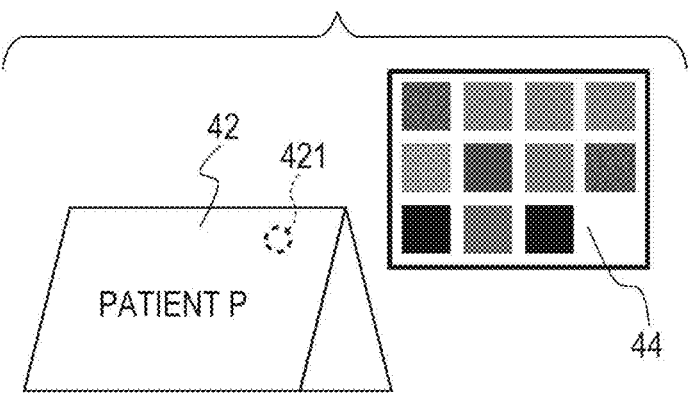

FIG. 4D illustrates the ID tag 42 intended to be disposed adjacent to the patient P and an example of a reference color sample set 44. The reference color sample set 44 can be used in a case where the image capturing apparatus 1 computes a white balance correction value for the first time and, for example, the base of the ID tag L is not white or the white base of the ID tag L has changed in color over time. In S305, the image capturing apparatus 1 captures an image of the ID tag 42 using a white balance correction value with which RGB brightness values of the reference color sample set 44 are corrected properly. An RGB brightness value of the white portion of the ID tag 42 acquired at this time is stored as a target value. After that, even if there is no reference color sample set 44, the image capturing apparatus 1 computes a white balance correction value, with which the RGB brightness value of the white portion 421 of the ID tag 42 is corrected to the target value acquired as described above, in S307. A white balance correction value that is more likely to be suitable for correction can be obtained in the above-described manner in the case where the white balance correction value is computed for the first time and, for example, the base of the ID tag L is not white or the white base has changed in color over time.

Furthermore, the image capturing apparatus 1 may determine whether the white balance correction value computed in S307 is outside a predetermined value range. If the white balance correction value is outside the predetermined value range, the image capturing apparatus 1 can inform the user that the white portion 421 of the ID tag 42 has a color that is not suitable for correction. In addition, the image capturing apparatus 1 performs storage control to record a flag indicating that the white balance correction value may not be suitable on metadata concerning the affected-area image acquired in S308. In this case, in S316, the image capturing apparatus 1 can display information indicating that the white balance correction value may not be suitable together with the affected-area image on the display 15.

Instead of or in addition to displaying the information indicating that the white balance correction value may not be suitable together with the affected-area image, for example, the following operations may be performed. In S307, the image capturing apparatus 1 associates the information indicating that the white balance correction value may not be suitable with the information concerning the patient P acquired in S305. In S313, the image processing apparatus 2 stores the information indicating that the white balance correction value may not be suitable and the information concerning the patient P associated with each other into the storage 24. After that, when receiving information concerning the patient P in S310, the image processing apparatus 2 determines whether the information indicating that the white balance correction value may not be suitable is stored in the storage 24 in association with the information concerning the same patient P. If the information indicating that the white balance correction value may not be suitable is stored in the storage 24 in association with the information concerning the same patient P, the image processing apparatus 2 transmits information indicating the above-described fact to the image capturing apparatus 1 in S314. In S316, the image capturing apparatus 1 displays information indicating that the ID tag L is to be replaced by a new one together with the affected-area image on the display 15 in response to receiving the information.

Figure 5:
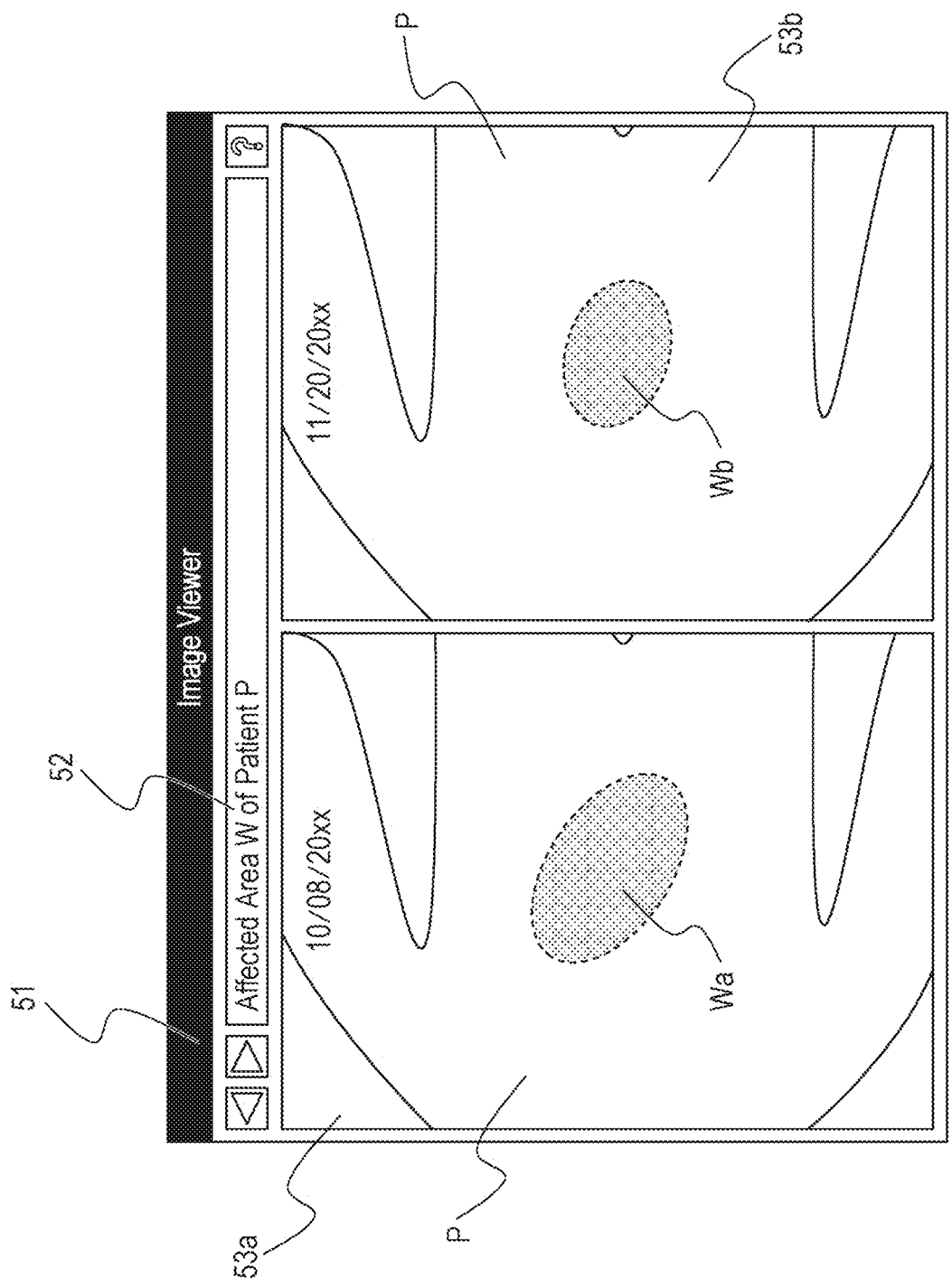
FIG. 5 is a diagram illustrating an example of a group of affected-area images displayed.

FIG. 5 illustrates an example of a group of affected-area images displayed side by side on the display apparatus 3. An exemplary manner in which a user views the group of affected-area images will now be described with reference to FIG. 5.

The display apparatus 3 is communicatively connected to the image processing apparatus 2. The display apparatus 3 displays an image viewer 51. The image viewer 51 includes an address bar 52 in which the user designates a patient P and an affected area W. The image processing apparatus 2 can extract images of the patient P and the affected area W designated in the address bar 52 from images stored in the storage 24. The image viewer 51 includes an image display region 53a and an image display region 53b. The image display region 53a displays a relatively old affected-area image. The image display region 53b displays a relatively new affected-area image. The old affected-area image includes an earlier affected area Wa. The new affected-area image includes a later affected area Wb. The above-described white balance correction based on the white portion of the ID tag allows the captured image of the earlier affected area Wa and that of the later affected area Wb to have substantially the same color tones. The user can compare the earlier affected area Wa with the later affected area Wb for accurate examination.

In the embodiment, as described above, the image capturing apparatus 1 captures an image of the ID tag L displaying the ID information of the patient P to acquire an ID-tag image, and obtains a color correction value for correction of an image to be captured from a region having a reference color in the ID-tag image. When capturing an image of the affected area W, the image capturing apparatus 1 corrects the captured image of the affected area W with the color correction value to acquire an affected-area image. Thus, it is unnecessary for the user to prepare a reference color sample set for correction. The color tones of an affected-area image can be reproduced for each image capture. This reduces a burden to the user and achieves reproduction of color tones of an affected-area image for each image capture.

In the embodiment, the image capturing apparatus 1 captures an image of the reference color sample set 44, and sets a color correction value so that colors of the reference color sample set 44 in the captured image of the reference color sample set 44 are close to colors of the actual reference color sample set 44. The image capturing apparatus 1 performs correction with the set color correction value when capturing an image of the ID tag L to acquire an ID-tag image, and stores an RGB brightness value of a white portion of the ID tag L as a target value. If the color of the ID tag L is not an intended color (white in the embodiment) or has changed over time, it is unnecessary for the user to prepare a reference color sample set for each image capture of the affected area W. The color tones of an affected-area image can be reproduced for each image capture.

In the embodiment, when a color correction value obtained from an ID-tag image is outside a reference range, the image capturing apparatus 1 informs the user that the color correction value may not be suitable. This reduces or eliminates the likelihood that the user may make a diagnosis based on, for example, an affected-area image having low reliability.

In the above-described exemplary embodiment, the image capturing apparatus 1 reads information on the ID tag, computes a white balance correction value, and displays an image obtained by superimposing the features of the affected area W on the captured affected-area image.

In some embodiments, the image capturing apparatus 1 captures an image of the ID tag and an image of the affected area W and transmits these raw images to the image processing apparatus 2. The image processing apparatus 2 performs the other processes. In some embodiments, the image capturing apparatus 1 captures an image of the ID tag and an image of the affected area W and computes a white balance correction value. The image processing apparatus 2 acquires these raw images and the white balance correction value and performs the other processes.

In some embodiments, any process of analyzing a captured image is performed by either the image capturing apparatus 1 or the image processing apparatus 2. In some embodiments, the processes are assigned to the image capturing apparatus 1 and the image processing apparatus 2 based on functions of these apparatuses. In some embodiments, the image capturing apparatus 1 alone carries out all of the processes, or capturing images, acquiring information concerning the patient P, computing a white balance correction value, performing white balance correction processing, extracting features of the affected area W, and displaying an image obtained by superimposing the features of the affected area W on a captured image.

It is to be understood that the above-described embodiments are intended to merely illustrate specific examples for implementing the disclosure, and should not be construed as limiting the technical scope of the disclosure. In other words, the aspect of the embodiments can be implemented in various ways without departing from technical idea or main features of the aspect of the embodiments.

For example, a white balance correction value can be computed based on a white portion of a product tag assigned to each flower in a flower market, and an image of the flower can be captured using the computed white balance correction value. Thus, color tones of the flowers can be compared with each other under predetermined conditions regardless of place and time.

For example, a white balance correction value can be computed based on a tag assigned to each part or each product in a factory, and an image of the part or the product can be captured using the computed white balance correction value. Thus, whether the part or the product has a defect in color tone can be determined under predetermined conditions regardless of position of a production line.

OTHER EMBODIMENTS

Embodiment(s) of the disclosure can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2018-230778, filed Dec. 10, 2018, which is hereby incorporated by reference herein in its entirety.

What is claimed is:

1. An image capturing apparatus comprising:
   an image sensor; and
   a controller that acquires a first color correction value based on a first image captured by the image sensor, and
   corrects a second image captured by the image sensor with the first color correction value,
   wherein the first image includes an ID tag assigned to a subject,
   the second image is different from the first image and includes the subject, and
   the controller identifies first information in the ID tag included in the first image to acquire second information concerning the subject, extracts a region having a reference color in the first image based on a position of the first information, and computes the first color correction value based on the reference color of the extracted region.

2. The image capturing apparatus according to claim 1, wherein the controller acquires a second color correction value based on a reference color sample set in a third image captured by the image sensor, and
   corrects the first color correction value by using the second color correction value.

3. The image capturing apparatus according to claim 1, wherein the controller cause a display to display information indicating that the first color correction value is outside a reference range, in a case where the first color correction value is outside the reference range.

4. The image capturing apparatus according to claim 1, wherein the controller associates information indicating that the first color correction value is outside a reference range with the second image and store the information associated with the second image, in a case where the first color correction value is outside the reference range.

5. The image capturing apparatus according to claim 1, wherein the reference color is white.

6. The image capturing apparatus according to claim 1, wherein the subject is an affected area of a patient.

7. A method comprising:
acquiring a first color correction value based on a first image;
correcting a second image with the first color correction value, wherein the first image includes an ID tag assigned to a subject, the second image is different from the first image and includes the subject;
identifying first information in the ID tag included in the first image to acquire second information concerning the subject;
extracting a region having a reference color in the first image based on a position of the first information; and
computing the first color correction value based on the reference color of the extracted region.

8. The method according to claim 7, further comprising:
displaying, information indicating that the first color correction value is outside a reference range, in a case where the first color correction value is outside the reference range.

9. The method according to claim 7, further comprising:
associating information indicating that the first color correction value is outside the reference range with the second image; and
storing the information associated with the second image, in a case where the first color correction value is outside the reference range.

10. A nonvolatile storage medium storing a program that causes a computer to execute a method, the method comprising:
acquiring a first color correction value based on a first image; and
correcting a second image with the acquired first color correction value, wherein the first image includes an ID tag assigned to a subject, the second image is different from the first image and includes the subject;
identifying first information in the ID tag included in the first image to acquire second information concerning the subject;
extracting a region having a reference color in the first image based on a position of the first information; and
computing the first color correction value based on the reference color of the extracted region.

11. The nonvolatile storage medium according to claim 10, further comprising:
displaying, information indicating that the first color correction value is outside a reference range, in a case where the first color correction value is outside the reference range.

12. The nonvolatile storage medium according to claim 10, further comprising:
associating information indicating that the first color correction value is outside the reference range with the second image; and
storing the information associated with the second image, in a case where the first color correction value is outside the reference range.

* * * * *